US012604663B2

(12) United States Patent
Lu et al.

(10) Patent No.: US 12,604,663 B2
(45) Date of Patent: Apr. 14, 2026

(54) DOUBLE-CAPPED MICROMOLECULE ELECTRON DONOR MATERIAL AND PREPARATION AND APPLICATION THEREOF

(71) Applicant: Chongqing institute of green and intelligent technology, Chinese Academy of Sciences, Chongqing (CN)

(72) Inventors: Shirong Lu, Chongqing (CN); Ke Yang, Chongqing (CN); Qianqian Chen, Chongqing (CN); Dingqin Hu, Chongqing (CN); Tainan Duan, Chongqing (CN); Haiyan Chen, Chongqing (CN)

(73) Assignee: Chongqing institute of green and intelligent technology, Chinese Academy of Sciences, Chongqing (CN)

( * ) Notice: Subject to any disclaimer, the term of this patent is extended or adjusted under 35 U.S.C. 154(b) by 605 days.

(21) Appl. No.: 18/098,506

(22) Filed: Jan. 18, 2023

(65) Prior Publication Data

US 2023/0397496 A1 Dec. 7, 2023

(30) Foreign Application Priority Data

Jun. 7, 2022 (CN) ......................... 202210639645.4

(51) Int. Cl.
*H10K 85/60* (2023.01)
*C07D 495/22* (2006.01)
*H10K 30/30* (2023.01)

(52) U.S. Cl.
CPC ......... *H10K 85/6576* (2023.02); *H10K 30/30* (2023.02); *H10K 85/655* (2023.02); *C07D 495/22* (2013.01)

(58) Field of Classification Search
CPC ... H10K 85/6576; H10K 85/655; H10K 30/30
See application file for complete search history.

(56) References Cited

U.S. PATENT DOCUMENTS

2023/0397496 A1* 12/2023 Lu ...................... H10K 85/6576

* cited by examiner

*Primary Examiner* — Lindsey A Buck
(74) *Attorney, Agent, or Firm* — Cooper Legal Group, LLC

(57) ABSTRACT

Disclosed is a double-capped micromolecule electron donor material, its preparation and application. The micromolecule electron donor material comprises a molecular structure as shown in formula (I). The double-capped micromolecule electron donor material of the application has good solubility, stability, photoelectric property and solution processability, and may be used as an electron donor material for all-micromolecule organic solar cells.

10 Claims, 4 Drawing Sheets

4, DED-O, R= 1-octyl
5, DED-E, R= 2-ethylhexyl

1

2

3

4 or 5

DED-O

DED-E

4, DED-O, R= 1-octyl
5, DED-E, R= 2-ethylhexyl

DOUBLE-CAPPED MICROMOLECULE ELECTRON DONOR MATERIAL AND PREPARATION AND APPLICATION THEREOF

CROSS-REFERENCE TO RELATED APPLICATIONS

This application claims priority to Chinese Patent Application No. 202210639645.4, filed on Jun. 7, 2022, the contents of which are hereby incorporated by reference.

TECHNICAL FIELD

The application relates to the technical field of solar cells, and in particular to a double-capped micromolecule electron donor material, its preparation and application.

BACKGROUND

As a kind of flexible printable solar cell, the organic solar cell is composed of organic semiconductor materials as the core part, which has the advantages of wide sources of raw materials, good flexibility, solution treatment and printability. In recent years, organic solar cells have become one of the research hotspots in the industry. In recent two years, organic solar cells have developed rapidly, and the photoelectric conversion efficiency of all-small-molecule organic photovoltaic devices with non-fullerene as acceptor materials has exceeded 16%. However, non-fullerene electron acceptor materials are more expensive than fullerene, and non-Fuller organic solar cells are sensitive to film thickness, so they are not suitable for large-scale printing applications and market promotion.

The marketed micromolecule electron donor materials BTR, BTR-Cl, S1, S2, etc. based on BDT core have good solubility and stability. Although the photoelectric conversion efficiency of the system composed of BTR and fullerene electron acceptor $PC_{71}BM$ is better, the obtained efficiency is far less than that of non-fullerene electron acceptor, mainly because the phase separation morphology of the active layer is not excellent enough. Optimization strategies of donor materials based on BDT core mainly include core, thiophene π-bridge and end-capping; the optimization strategy of thiophene π-bridge has not achieved ideal results, while compared with the rapid development of polymer-micromolecule system, the donor materials based on BDT core and ring-expanded BDTT core progress slowly.

Therefore, it is of great scientific influence and practical significance to develop a brand-new capping structure or a brand-new capping type to improve its photoelectric conversion efficiency.

SUMMARY

In view of the above-mentioned shortcomings of the prior art, the objective of the present application is to provide a double-capped micromolecule electron donor material, its preparation and application. Through a brand-new structure design concept, a brand-new structure optimization route is created for the micromolecule electron donor material based on BDT core.

In order to achieve the above objective and other related objectives, the first aspect of the present application provides a double-capped micromolecule electron donor material, which includes a molecular structure as shown in formula (I):

(I)

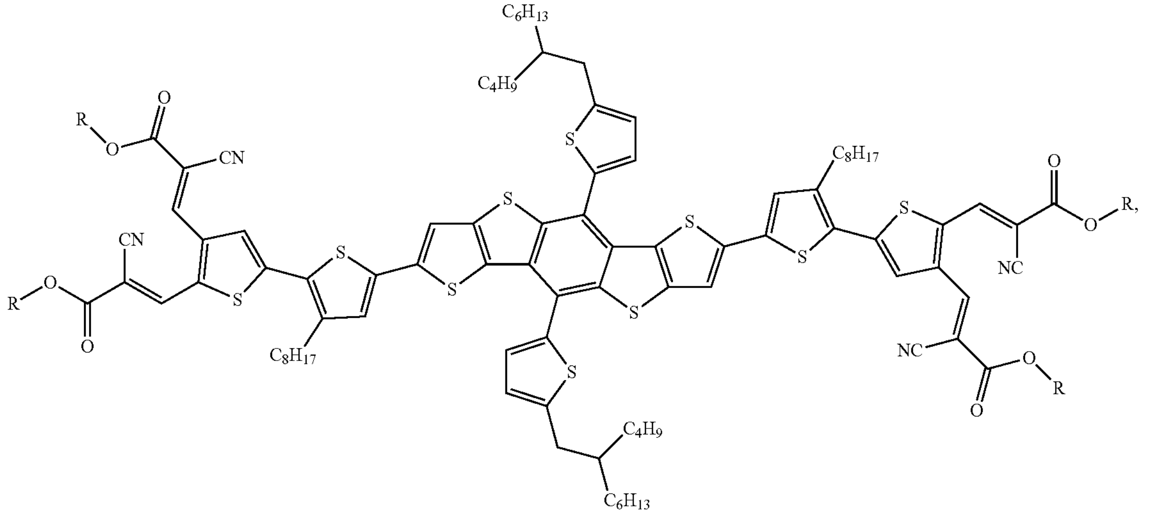

where R is any one of the following structures:

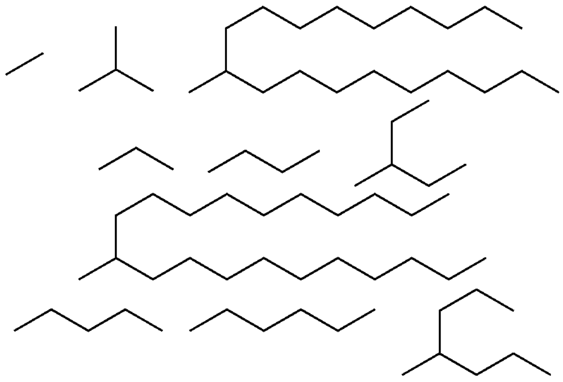

-continued
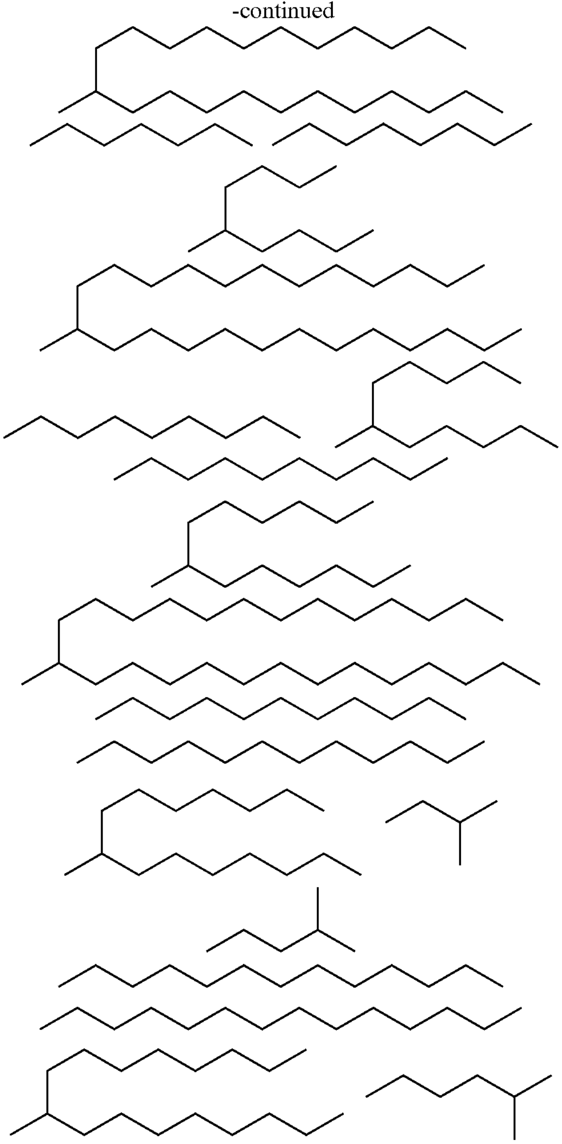
-continued
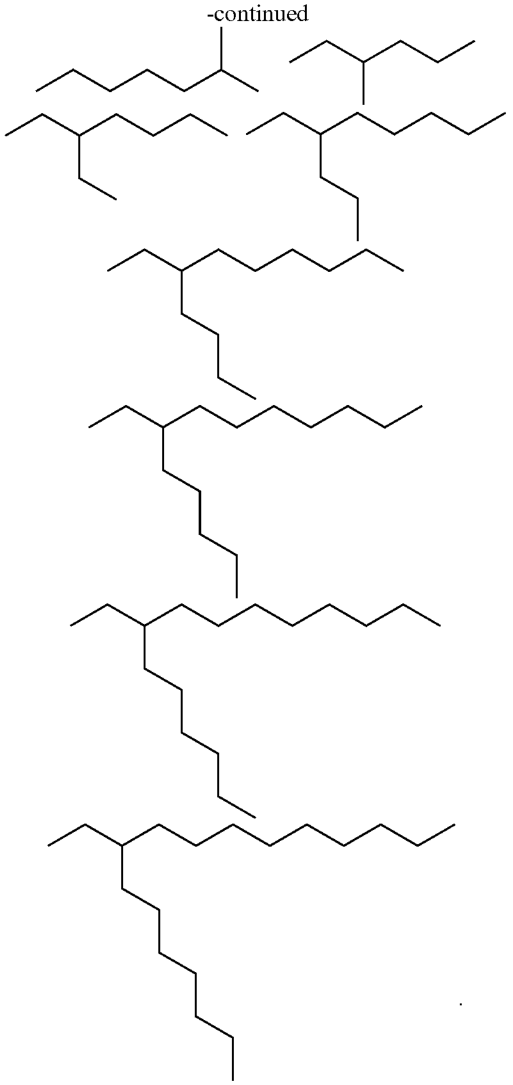
Optionally, the double-capped micromolecule electron donor material has a molecular structure as shown below:
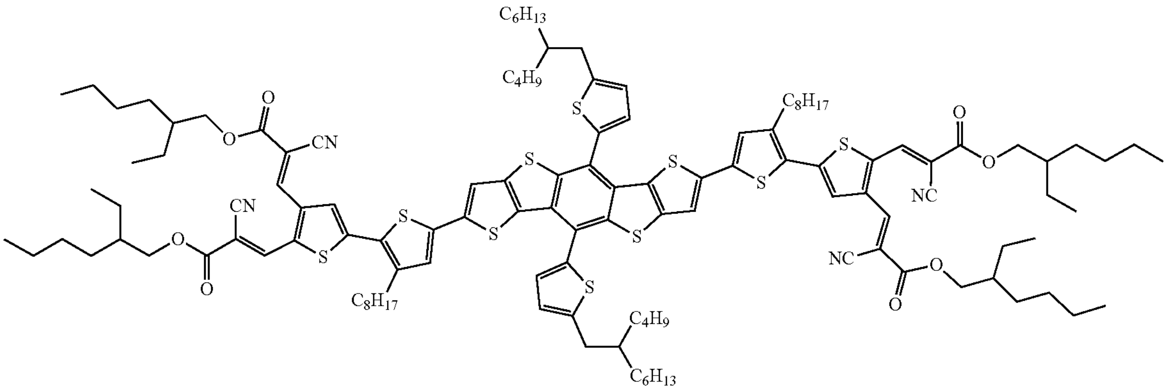
DED-E
or -continued

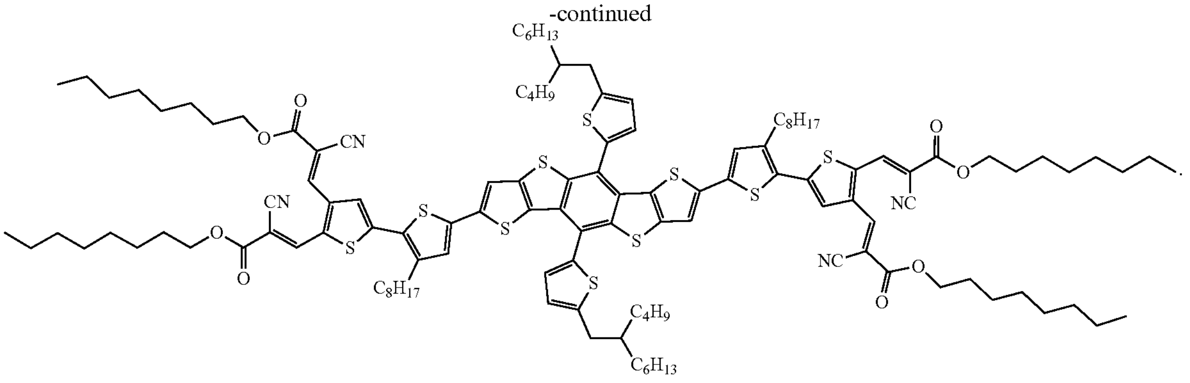

DED-O

The second aspect of the present application provides an active layer material for photovoltaic device, which includes the double-capped micromolecule electron donor material as described in the first aspect.

Optionally, the active layer material also includes an electron acceptor material.

Optionally, the electron acceptor material includes but is not limited to $PC_{71}BM$, Y6, IDIC and N3.

The third aspect of the present application provides a photovoltaic device containing the electron donor material as described in the first aspect or the active layer material as described in the second aspect.

Optionally, the photovoltaic device structure sequentially includes a substrate, a hole transport layer, an active layer containing the active layer material according to the second aspect, an electron transport layer and a metal electrode.

Optionally, the substrate includes transparent glass and a transparent conductive film.

Optionally, the hole transport layer is selected from at least one of PEDOT:PSS and $MoO_3$.

Optionally, the electron transport layer is selected from at least one of Phe-NaDPO, PDINO and PFBr.

Optionally, the thickness of the hole transport layer is 20-40 nm, specifically 20 nm, 25 nm, 30 nm, 35 nm and 40 nm.

Optionally, the thickness of the electron transport layer is 5-10 nm, specifically 5 nm, 6 nm, 7 nm, 8 nm, 9 nm and 10 nm.

Optionally, the thickness of the active layer is 80-200 nm, specifically 80 nm, 100 nm, 110 nm, 120 nm, 140 nm, 160 nm, 180 nm and 200 nm.

Optionally, the metal electrode is selected from any one of silver and aluminum.

Optionally, the photovoltaic device is an all-micromolecule solar cell.

All-micromolecules here mean that both the donor and acceptor of the active layer are micromolecules.

The fourth aspect of the present application provides the application of the double-capped micromolecule electron donor material as described in the first aspect or the active layer material as described in the second aspect in the preparation of photovoltaic devices.

The fifth aspect of the present application provides the preparation method of the double-capped micromolecule electron donor material as described in the first aspect, which includes the following steps: mixing and reacting dialdehyde compound with cyanoester to obtain an intermediate product, and then mixing and reacting the intermediate product with double tin alkylation reagent DTBDT to obtain the double-capped micromolecule electron donor material.

The molecular structure of the dialdehyde compound is as follows:

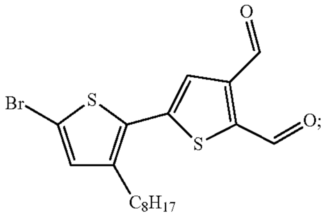

the molecular structure of the cyanoester is as follows:

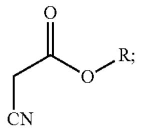

the molecular structure of the intermediate product is as follows:

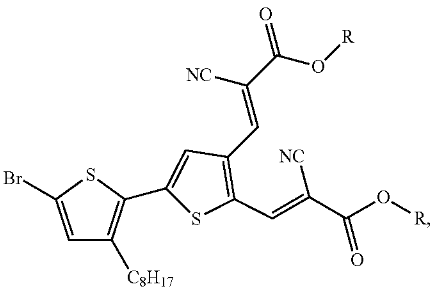

where R is any one of the following structures:

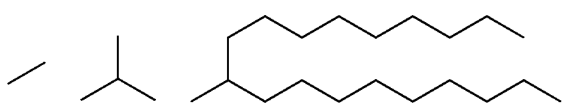

-continued

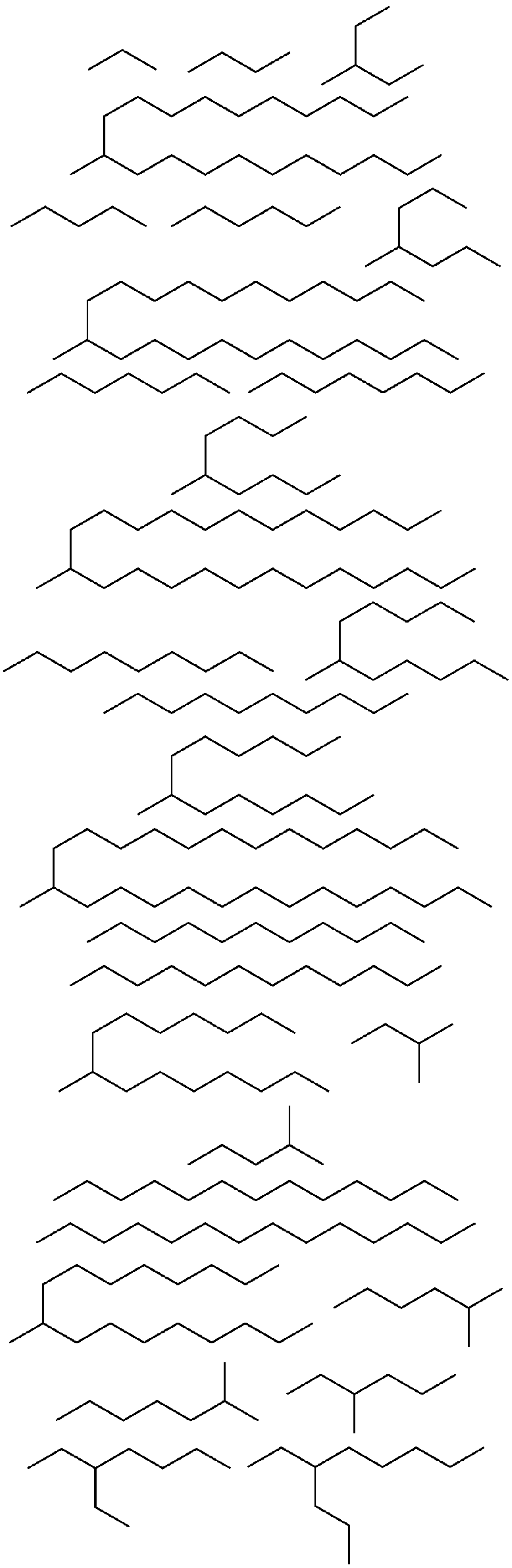

-continued

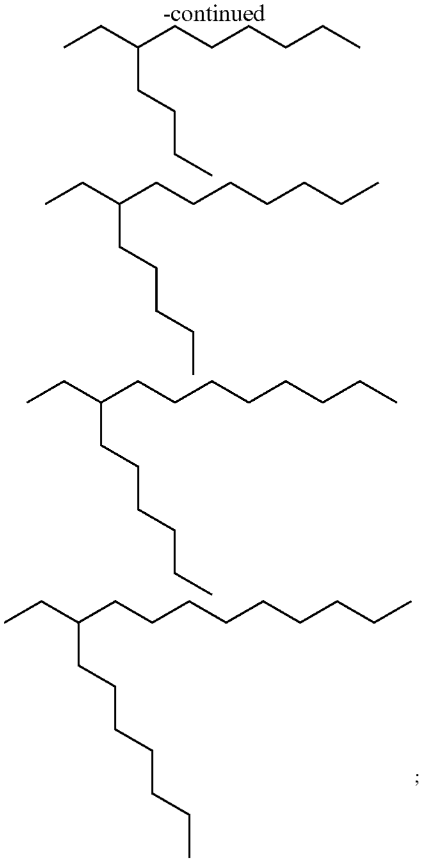

;

the molecular structure of the double tin alkylation reagent DTBDT is as follows:

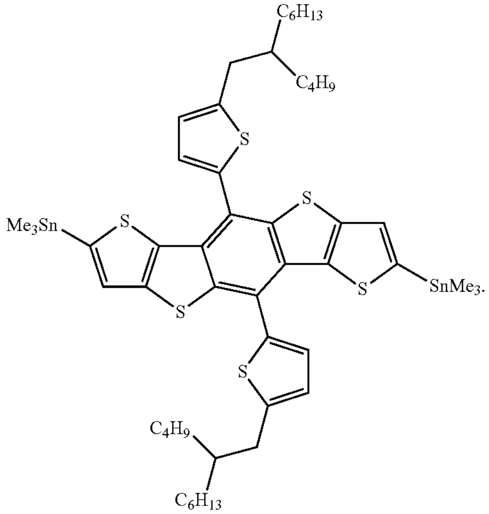

Optionally, the preparation method of the double-capped micromolecule electron donor material includes the following steps:

S1, mixing the dialdehyde compound, a solvent, the cyanoester and a catalyst, and reacting to obtain the intermediate product;

S2, mixing the intermediate product with the solvent, the double tin alkylation reagent DTBDT and the catalyst, and reacting to obtain the double-capped micromolecule electron donor material.

Optionally, in the S1, the molar ratio of the dialdehyde compound to the cyanoester is 1:(4-8).

Optionally, in the S1, the molar ratio of the dialdehyde compound to the catalyst is 1:(0.1-0.2).

Optionally, in the S1, the solvent includes but is not limited to chloroform, dichloromethane, toluene, tetrahydrofuran and acetic acid.

Optionally, in the S1, the catalyst is selected from at least one of alumina, piperidine, ammonium acetate and triethylamine.

Optionally, in the S1, the reaction temperature is 100-150° C. and the reaction duration is 4-10 h; the reaction temperature may be 100° C., 105° C., 110° C., 115° C., 120° C., 125° C., 130° C., 135° C., 140° C., 145° C., 150° C. and the reaction duration may be 4 h, 4.5 h, 5 h, 5.5 h, 6 h, 6.5 h, 7 h, 7.5 h, 8 h, 8.5 h, 9 h, 9.5 h, 10 h.

Optionally, in the S1, after the reaction is finished, the solvent is distilled off from the reaction solution under reduced pressure, and the intermediate product is obtained by silica gel column chromatography separation.

Optionally, in the S1, during silica gel column chromatography separation, the eluent is chloroform/petroleum ether mixture. Preferably, by volume, chloroform/petroleum ether is 1:1 in the chloroform/petroleum ether mixture.

Optionally, in the S2, the molar ratio of the intermediate product to the double tin alkylation reagent DTBDT is (2.0-2.5): 1.

Optionally, in the S2, the molar ratio of the intermediate product to the catalyst is 1:(0.1-0.2).

Optionally, in the S2, the solvent includes but is not limited to dioxane, toluene, chlorobenzene and o-xylene.

Optionally, in the S2, the catalyst is selected from at least one of tetrapalladium (triphenylphosphine), tridibenzylideneacetone dipalladium and 1,1'-bis diphenyl phosphine ferrocene palladium dichloride.

Optionally, in the S2, the reaction temperature is 100-200° C. and the reaction duration is 12-72 h; the reaction temperature may be 100° C., 105° C., 110° C., 115° C., 120° C., 125° C., 130° C., 135° C., 140° C., 145° C., 150° C., 155° C., 160° C., 165° C., 170° C., 170° C., 180° C., 200° C.; the reaction duration may be 12 h, 13 h, 14 h, 15 h, 16 h, 17 h, 18 h, 19 h, 20 h, 21 h, 22 h, 23 h, 24 h, 25 h, 26 h, 27 h, 28 h, 29 h, 30 h, 35 h, 40 h, 45 h, 50 h, 55 h, 60 h, 65 h, 70 h and 72 h.

Optionally, in the S2, after the reaction is finished, the solvent is distilled off from the reaction solution under reduced pressure, and the intermediate product is obtained by silica gel column chromatography separation.

Optionally, in the S2, the eluent is chloroform/petroleum ether mixture during silica gel column chromatography separation; optionally, in the chloroform/petroleum ether mixture, the ratio of chloroform to petroleum ether is 3:1 by volume.

As mentioned above, the double-capped micromolecule electron donor material, its preparation and application of the present application have the following beneficial effects.

The double-capped micromolecule electron donor material provided by the application has good solubility, stability, photoelectric property and solution processability, and may be used as an electron donor material for all-micromolecule organic solar cells; compared with the traditional single-capping and asymmetric-capping micromolecule donors, the double-capped micromolecule electron donor material of the present application may form a better phase separation morphology with micromolecule acceptors, and has a good photoelectric conversion efficiency of organic solar cells, and provides a brand-new capping design concept of donor micromolecules, opening up a brand-new road for the structural design of donor micromolecule materials. The application has great application potential and value in the fields of organic solar cells and related photovoltaics.

DETAILED DESCRIPTION OF THE EMBODIMENTS

The following specific examples illustrate the embodiments of the present application, and those skilled in the art may easily understand other advantages and efficacy of the present application from the disclosure of this specification. The application may also be implemented or applied by other different specific embodiments, and the details in this specification may be modified or changed based on different viewpoints and applications without departing from the spirit of the application. It should also be understood that the following embodiments of specific process parameters are only one example of the appropriate range, and those skilled in the art may make choices within the appropriate range through the description herein, and are not limited to the specific values in the following embodiments.

In the following embodiments, indium tin oxide (ITO) is selected as the cathode material, poly (3,4-ethylenedioxythiophene):poly (styrene sulfonate) (PEDOT:PSS) is selected as the hole transport layer, the acceptor in the active layer is Y6, and the electron transport layer is selected as phenyl (2-naphthyl) diphenyl phosphine oxide (Phe-NaDPO), and Ag is selected as cathode material.

Figure 2:
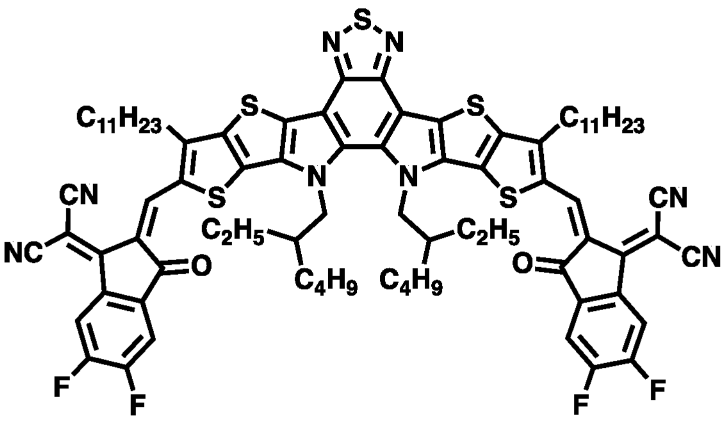
FIG. 2 is a schematic diagram of the molecular structure of electron acceptor material Y6 used in Embodiment 3 and Embodiment 4 of the present application.

In the following embodiments, ITO is purchased from a preferred technology company, and Clevios AL4083 is used as PEDOT:PSS; Y6 is purchased from Ruixun, and its structural formula is shown in FIG. 2; Phe-NaDPO is purchased from 1 Material Tech Inc. Other raw materials and reagents that are not indicated by the way of purchase may be purchased from the market.

Embodiment 1

Figure 1:
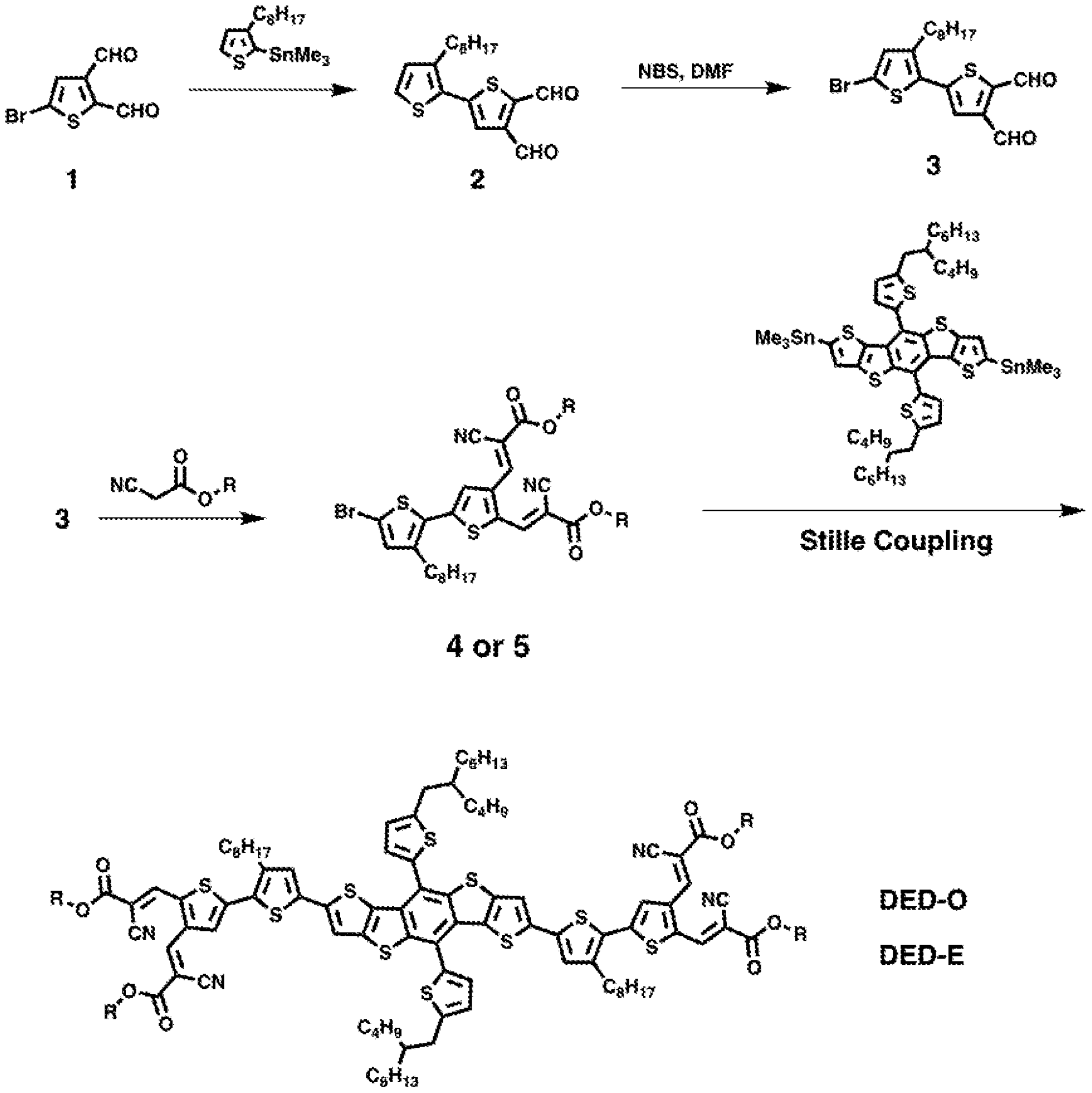
FIG. 1 is a road map for the synthesis of double-capped micromolecule electron donor materials in Embodiment 1 and Embodiment 2 of the present application.

As shown in FIG. 1, the preparation process of DED-E, a double-capped micromolecule electron donor material in this embodiment, is as follows:

1. Synthesis of Compound 4

Compound 3 (0.3000 g, 0.7257 mmol, made by Gia, or self-made in the laboratory according to the synthetic route shown in FIG. 1) and cyanoester (0.859 g, 4.354 mmol from Gia) are dissolved in 50 ml of anhydrous toluene, and then 800 mg of alkaline $Al_2O_3$ powder is added, followed by stirring at 110° C. for 6 h. Then the solvent is removed under reduced pressure and separated by silica gel column chromatography. The eluent is chloroform/petroleum ether (by volume, chloroform:petroleum ether=1:1), and the product compound 4 is a viscous red solid (0.476 g, the yield is 85% of the theoretical yield).

Characterization data of compound 4: 1H NMR (400 MHz, CDCl3, δ ppm): 8.50 (s, 1H), 8.41 (s, 1H), 8.13 (s, 1H), 6.98 (s, 1H), 4.28-4.25 (m, 4H), 2.81-2.78 (t, J=7.6 Hz, 2H), 1.75-1.62 (m, 4H), 1.47-1.26 (m, 26H), 0.95-0.85 (m, 15H). 13C NMR (101 MHz, CDCl3, δ ppm): 162.21, 161.79, 144.18, 143.93, 141.93, 140.38, 139.77, 138.73, 133.67, 129.51, 124.88, 115.30, 114.86, 114.68, 106.39, 101.72, 69.62, 69.39, 38.83, 38.80, 31.83, 30.34, 29.72, 29.34, 29.32, 29.14, 28.93, 23.79, 22.92, 22.64, 14.08, 14.02, 11.02.

2. Synthesis of Compound DED-E:

Compound 4 (0.3000 g, 0.3886 mmol) and DTBDT alkylated with bistin (0.1828 g, mmol from Kyrgyzstan) are dissolved in 50 ml of toluene, and then 150 mg of Pd (PPh3)4 (tetratriphenylphosphine palladium) is added. Stir at 110° C. for 48 h. Then the solvent is removed under reduced pressure and separated by silica gel column chromatography. The eluent is chloroform/petroleum ether (by volume, chloroform:petroleum ether=3:1), and the product DED-E is a black solid (0.283 g, the yield is 80% of the theoretical yield).

Characterization data of compound DED-E: 1H NMR (400 MHz, CDCl3, δ ppm): 8.48 (s, 2H), 8.41 (s, 2H), 8.17 (s, 2H), 7.35 (s, 2H), 7.23 (d, J=3.6 Hz, 2H), 7.05 (d, J=3.6 Hz, 2H), 7.00 (s, 2H), 4.31-4.20 (m, 8H), 2.99 (d, J=6.8 Hz, 4H), 2.85 (t, J=7.6 Hz, 4H), 1.83-1.67 (m, 1.48-1.26 (m, 84H), 0.98-0.85 (m, 42H). 13C NMR (101 MHz, CDCl3, δ ppm): 162.36, 161.83, 147.24, 144.91, 144.76, 143.41, 142.03, 140.17, 140.00, 139.90, 139.68, 138.78, 138.04, 133.99, 133.26, 130.09, 128.68, 127.52, 126.15, 124.15, 123.74, 117.20, 115.47, 114.92, 106.21, 100.83, 69.61, 69.34, 40.06, 38.85, 34.63, 33.41, 32.96, 31.97, 31.90, 30.37, 30.24, 29.78, 29.56, 29.48, 29.25, 28.95, 28.90, 26.69, 23.83, 23.16, 22.95, 22.72, 22.69, 14.25, 14.14, 14.12, 14.03, 11.03. HR-MS (+APCI, m/z): calcd. for C126H167N4O8S10+[M+H]+: 2183.99855, found 2183.99855.

Embodiment 2

As shown in FIG. 1, the preparation process of DED-O, a double-capped micromolecule electron donor material in this embodiment, is as follows:

1. Synthesis of Compound 5

Compound 3 (0.3000 g, 0.7257 mmol made by Gia) and cyanoester (0.859 g, 4.354 mmol from Gia) are dissolved in 50 ml of anhydrous toluene, and then 800 mg of alkaline $Al_2O_3$ powder is added. Stir at 110° C. for 6 h. Then the solvent is removed under reduced pressure and separated by silica gel column chromatography. The eluent is chloroform/petroleum ether (by volume, chloroform:petroleum ether=1:1), and the product compound 5 is a viscous red solid (0.476 g, the yield is 85% of the theoretical yield).

Characterization data of compound 5: 1H NMR (400 MHz, CDCl3, δ ppm): 8.50 (s, 1H), 8.41 (s, 1H), 8.12 (s, 1H), 6.98 (s, 1H), 4.37-4.31 (m, 4H), 2.81 (t, J=7.6 Hz, 2H), 1.80-1.75 (m, 4H), 1.66-1.63 (m, 2H), 1.42-1.26 (m, 30H), 0.90-0.85 (m, 9H). 13C NMR (101 MHz, CDCl3, δ ppm): 162.16, 161.73, 144.19, 143.96, 142.00, 140.45, 139.77, 138.71, 133.67, 129.49, 124.89, 115.35, 114.89, 114.68, 106.42, 101.73, 67.40, 67.18, 31.82, 31.75, 30.34, 29.73, 29.33, 29.13, 28.50, 28.47, 25.76, 22.61, 14.05.

2. Synthesis of Compound DED-O:

Compound 5 (0.3000 g, 0.3886 mmol) is dissolved in 50 ml of toluene with DTBDT (0.1828 g, 0.1619 mmol from Kyrgyzstan) alkylated with bistin, and then 150 mg of Pd(PPh3)4 (tetratriphenylphosphine palladium) is added. Stir at 110° C. for 48 h. Then the solvent is removed under reduced pressure and separated by silica gel column chromatography. The eluent is chloroform/petroleum ether (by volume, chloroform:petroleum ether=3:1), and DED-O is a black solid (0.283 g, the yield is 80% of the theoretical yield).

Characterization data of compound DED-O: 1H NMR (400 MHz, CDCl3, δ ppm): 8.46 (s, 2H), 8.39 (s, 2H), 8.15 (s, 2H), 7.32 (s, 2H), 7.23 (d, J=3.2 Hz, 2H), 7.05 (d, J=3.2 Hz, 2H), 6.98 (s, 2H), 4.36-4.29 (m, 8H), 2.99 (d, J=6.4 Hz, 4H), 2.84 (t, J=7.6 Hz, 4H), 1.82-1.64 (m, 14H), 1.45-1.29 (m, 92H), 0.94-0.84 (m, 30H). 13C NMR (101 MHz, CDCl3, δ ppm): 162.29, 161.77, 147.22, 144.89, 144.75, 143.42, 142.05, 140.16, 139.97, 139.88, 139.58, 138.72, 137.92, 133.97, 133.20, 130.00, 128.71, 127.47, 126.13, 124.02, 123.67, 117.13, 115.54, 114.97, 106.16, 100.66, 67.35, 67.07, 40.06, 34.64, 33.42, 32.95, 31.98, 31.92, 31.80, 30.33, 29.79, 29.59, 29.50, 29.27, 29.21, 29.18, 28.88, 28.55, 28.53, 26.70, 25.82, 23.17, 22.73, 22.70, 22.66, 14.26, 14.14, 14.13, 14.09. HR-MS (+APCI, m/z): calcd. for C126H167N408S10+[M+H]+: 2183.99855, found 2183.99855.

Embodiment 3

The double-capped micromolecule electron donor material (DED-E shown in FIG. 1) prepared in Embodiment 1 is used to prepare an all-micromolecule organic solar cell. The specific preparation process is as follows:

Ultrasonic cleaning the substrate composed of transparent glass and transparent conductive electrode ITO with cleaning solution, deionized water, acetone and isopropanol, and blowing it with nitrogen after cleaning; after the substrate is treated in an ozone cleaner for 15 min, the hole transport layer material PEDOT:PSS (4000 rpm, 20 s, film thickness 30 nm) is spin-coated in the air, and then it is thermally annealed in the air (120° C., 10 min), and then the sample is sent into a glove box filled with nitrogen. The active layer (DED-E:Y6=2:1, 40 mg/ml, active layer film thickness≈200 nm) is prepared on PEDOT:PSS hole transport layer by spin coating method, and the obtained active layer film is subjected to solvent annealing treatment (CF, 30 s) in glove box. Then, the electron transport layer DPO (2000 rpm, 10 s, film thickness 8 nm) is spin-coated on the active layer, and then the Ag electrode (film thickness 100 nm) is vapor-deposited on the electron transport layer, and the solar cell is manufactured.

Embodiment 4

The double-capped micromolecule electron donor material (DED-O shown in FIG. 1) prepared in Embodiment 2 is used to prepare an all-micromolecule organic solar cell. The specific preparation process is as follows:

Ultrasonic cleaning the substrate composed of transparent glass and transparent conductive electrode ITO with cleaning solution, deionized water, acetone and isopropanol, and blowing it with nitrogen after cleaning; after the substrate is treated in an ozone cleaner for 15 min, the hole transport layer material PEDOT:PSS (4000 rpm, 20 s, film thickness 30 nm) is spin-coated in the air, and then it is thermally annealed in the air (120° C., 10 min), and then the sample is sent into a glove box filled with nitrogen. The active layer (DED-O:Y6=2:1, 40 mg/ml, active layer film thickness≈200 nm) is prepared by spin coating on PEDOT:PSS hole transport layer, and the obtained active layer film is subjected to solvent annealing treatment (CF, 30 s) in glove box. Then, the electron transport layer DPO (2000 rpm, 10 s, film thickness 8 nm) is spin-coated on the active layer, and then the Ag electrode (film thickness 100 nm) is vapor-deposited on the electron transport layer, and the solar cell is manufactured.

Figure 3:
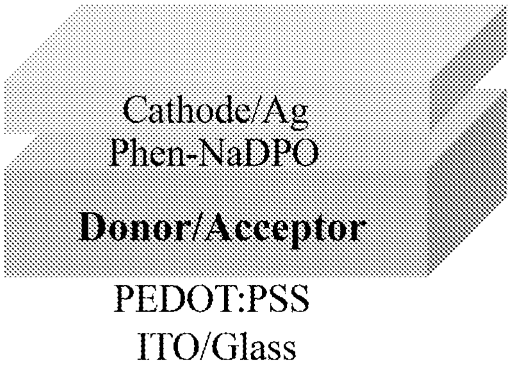
FIG. 3 is a schematic diagram of the structure of all-molecule organic solar cell devices in Embodiment 3 and Embodiment 4 of the present application.

The structures of organic solar cells prepared in Embodiment 3 and Embodiment 4 are shown in FIG. 3.

Figure 4:
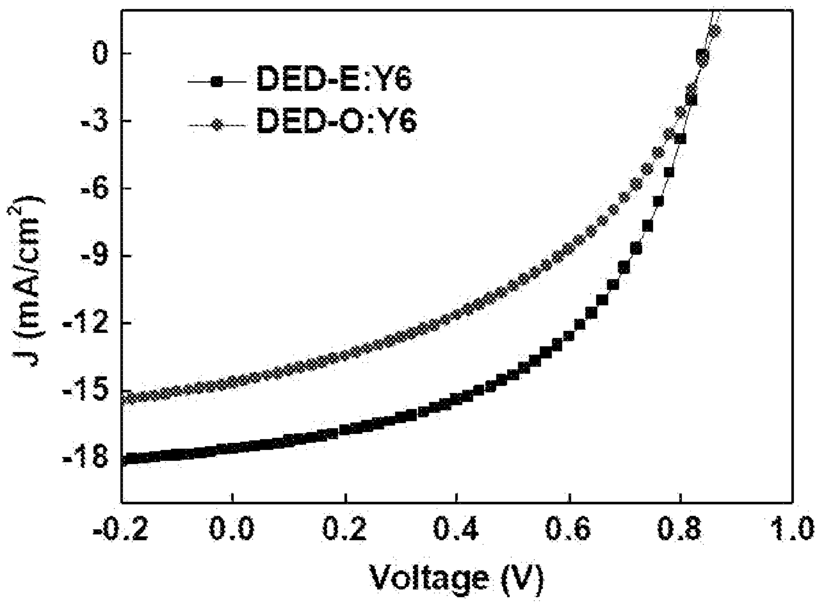
FIG. 4 shows the current density-voltage characteristic curves of the devices in Embodiment 3 (DED-E:Y6=2:1 40 mg/ml) and Embodiment 4 (DED-O:Y6=1.5:1 40 mg/ml) of the present application under standard test conditions (AM1.5, 100 mW/cm$^2$).

The light J-V curves of the organic solar cells obtained in Embodiment 3 and Embodiment 4 are shown in FIG. 4, and the light J-V photovoltaic performance parameters are shown in Table 1:

TABLE 1

| | Condition | $V_{oc}$ (V) | $J_{sc}$ (mA/cm$^2$) | FF (%) | PCE (%) |
|---|---|---|---|---|---|
| Embodiment 3 | SVA = CF/30 s | 0.83 | 17.17 | 49.58 | 7.53 (7.26 ± 0.09) |
| Embodiment 4 | SVA = CF/30 s | 0.84 | 14.63 | 41.52 | 5.26 (5.13 ± 0.12) |

In Table 1, SVA represents solvent annealing, Voc represents voltage, Jsc represents short-circuit current density, FF represents filling factor, and PCE represents photoelectric conversion efficiency.

As can be seen from Table 1, when chloroform is used as the solvent and the annealing time is 30 s, the organic solar cells with double-capped micromolecule electron donor DED-E with 2-ethylhexyl carbon chain as R group and DED-O with n-octane carbon chain as R group as active layers all have good photoelectric conversion efficiency.

To sum up, the double-capped micromolecule electron donor material provided by the application has excellent repeatability and solution processability, and compared with the traditional single-capped micromolecule donor material, the organic solar cell prepared from it may also obtain relatively good photoelectric conversion efficiency; moreover, after changing the end-capped carbon chain of the micromolecule electron donor material, the organic solar cells made from it may still obtain relatively good photoelectric conversion efficiency, showing good universality; the film thickness of the active layer may reach 200 nm, which may be applied to the spin-coating and printing process of all-small organic solar cells. Of course, the double-capped micromolecule electron donor material is not limited to organic solar cells, but also applicable to other photovoltaic devices.

The above embodiments only illustrate the principle and efficacy of the present application, and are not intended to limit the present application. Anyone skilled in the art may modify or change the above embodiments without departing from the spirit and scope of the present application. Therefore, all equivalent modifications or changes made by those with ordinary knowledge in the technical field without departing from the spirit and technical idea disclosed by the present application should still be covered by the claims of the present application.

What is claimed is:

1. A double-capped micromolecule electron donor material, comprising a molecular structure shown in formula (I):

(I)

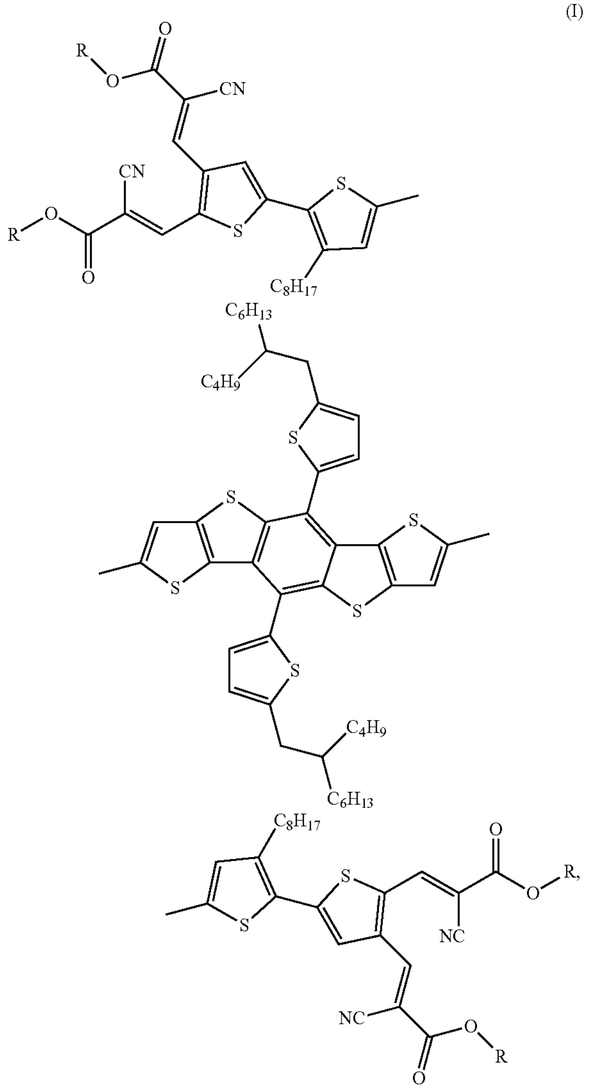

wherein R is any one of following structures:

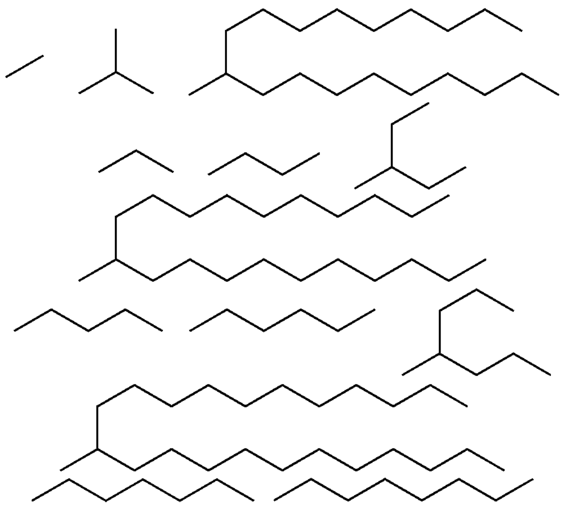

-continued
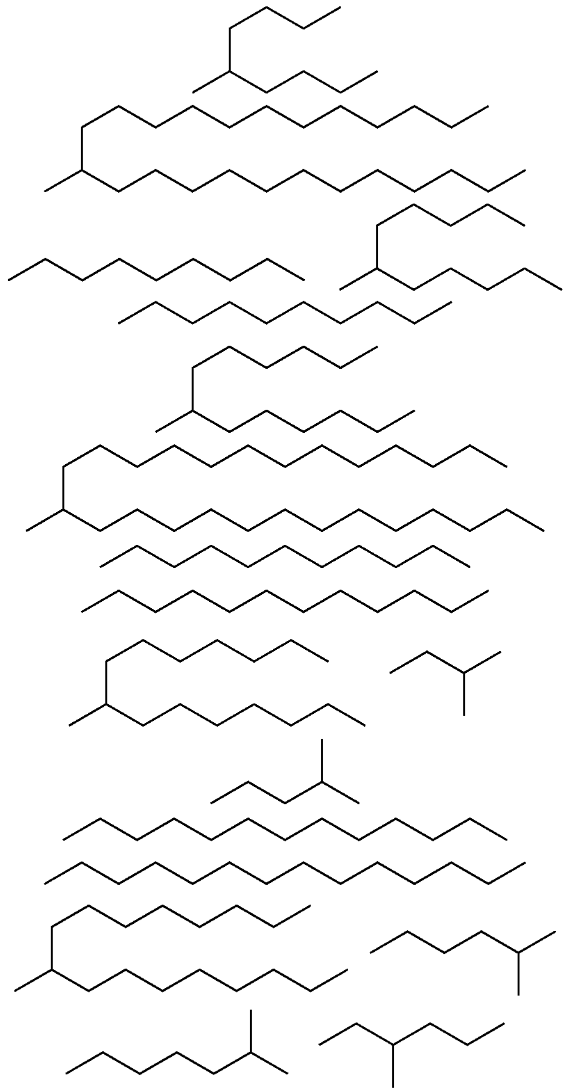
-continued
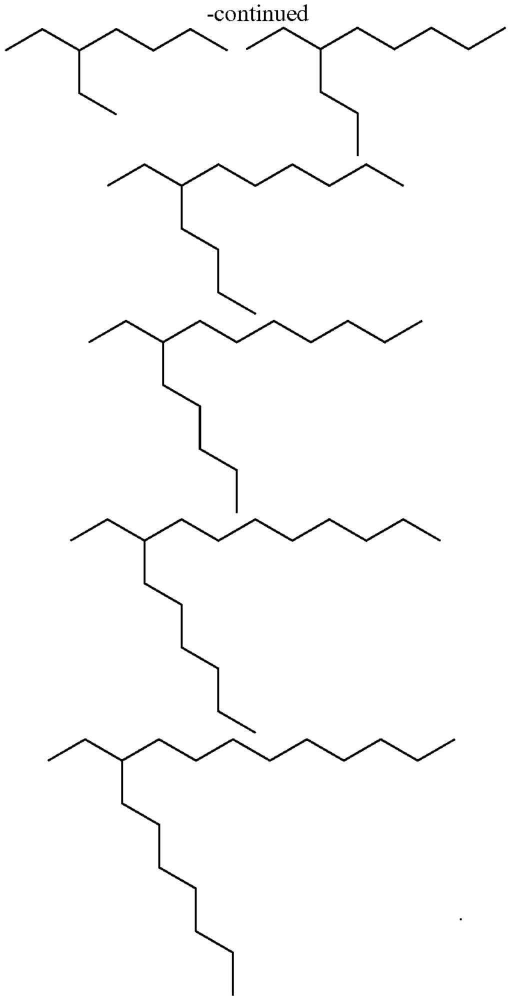
.
2. The double-capped micromolecule electron donor material according to claim 1, wherein the double-capped micromolecule electron donor material has a following molecular structure:
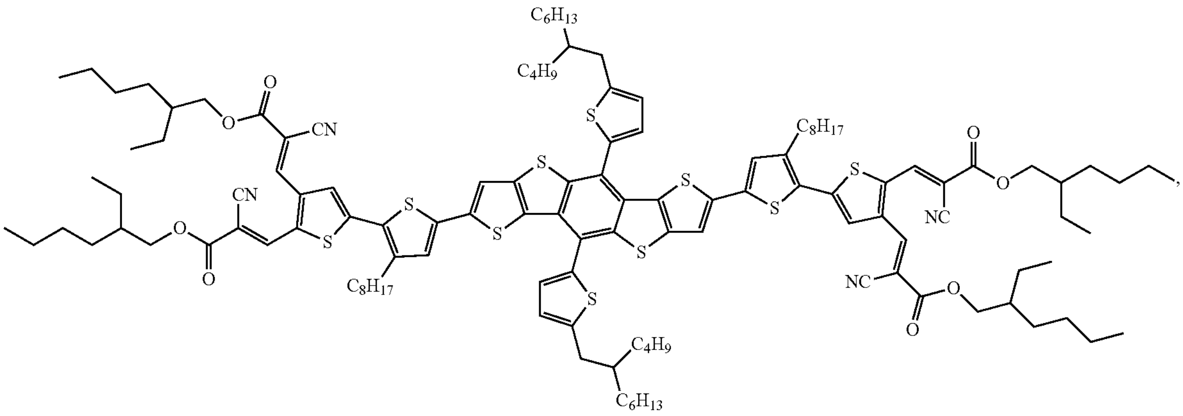
,
DED-E
or -continued

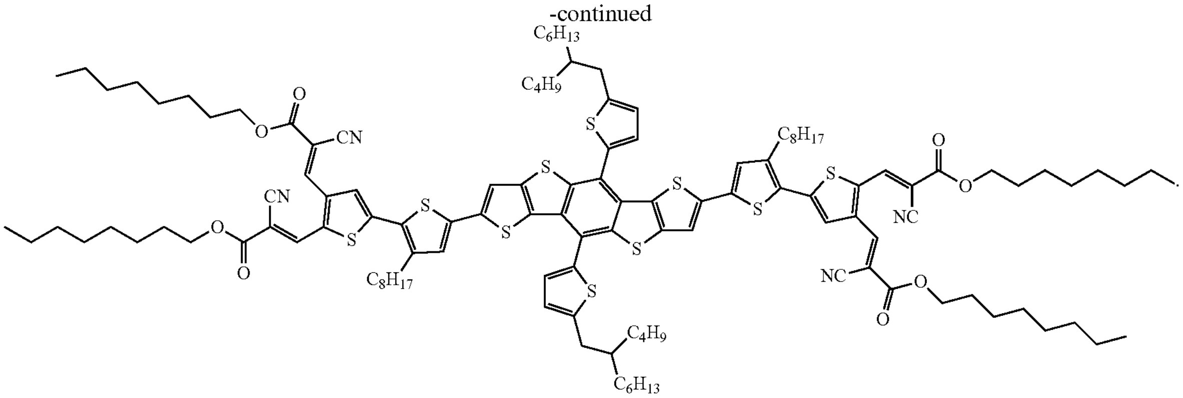

DED-O

3. An active layer material for photovoltaic devices, wherein the active layer material comprises the double-capped micromolecule electron donor material according to claim 1.

4. The active layer material according to claim 3, wherein the active layer material further comprises an electron acceptor material.

5. The active layer material according to claim 4, wherein the electron acceptor material is selected from any one of $PC_{71}BM$, Y6, IDIC and N3.

6. A photovoltaic device, comprising the double-capped micromolecule electron donor material according to claim 1.

7. A preparation method of the double-capped micromolecule electron donor material according to claim 1, comprising following steps: mixing and reacting dialdehyde compound with cyanoester to obtain an intermediate product, and then mixing and reacting the intermediate product with double tin alkylation reagent DTBDT to obtain the double-capped micromolecule electron donor material;

wherein a molecular structure of the dialdehyde compound is as follows:

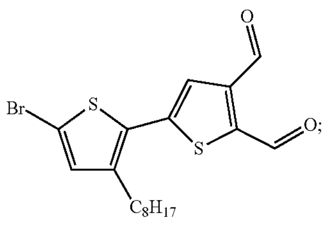

a molecular structure of the cyanoester is as follows:

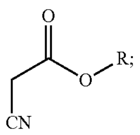

a molecular structure of the intermediate product is as follows:

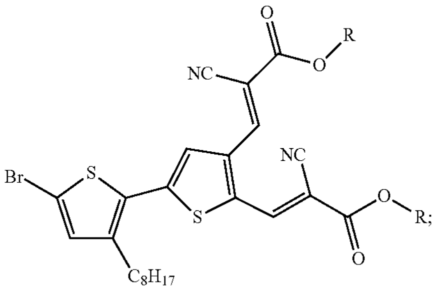

R is any one of following structures:

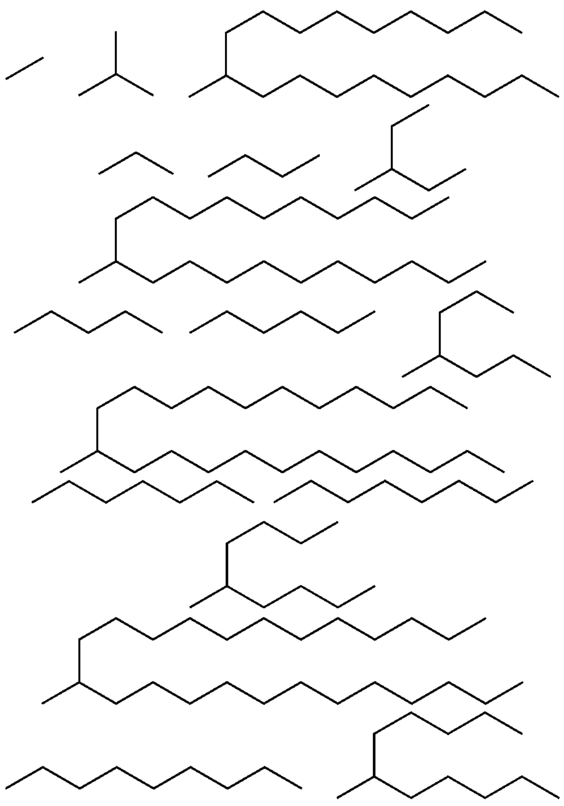

-continued

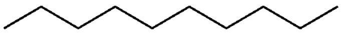

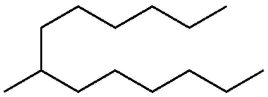

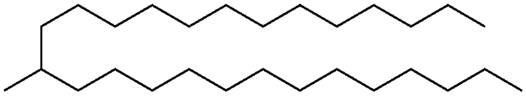

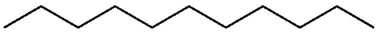

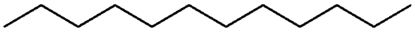

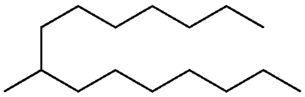

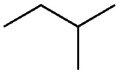

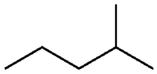

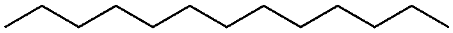

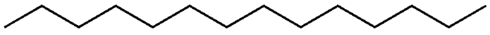

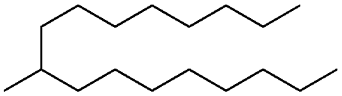

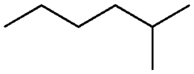

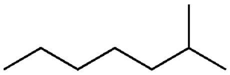

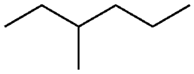

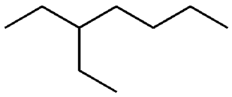

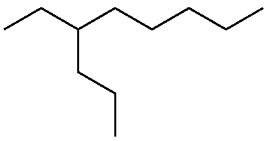

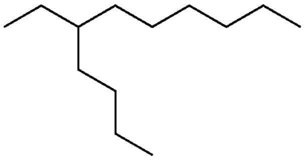

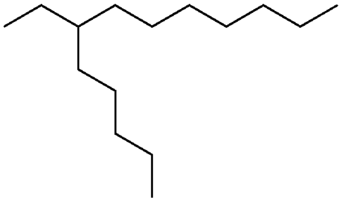

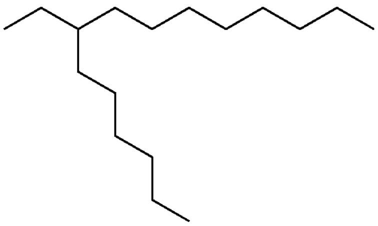

-continued

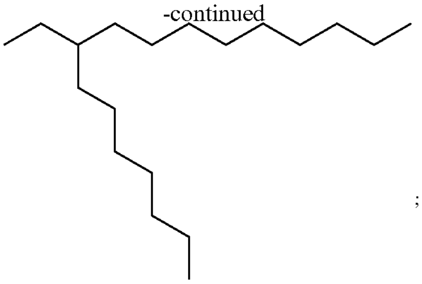

;

and a molecular structure of the double tin alkylation reagent DTBDT is as follows:

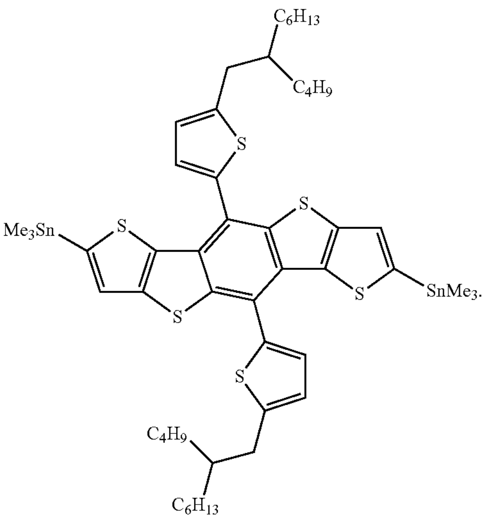

8. The preparation method according to claim 7, comprising:

S1, mixing the dialdehyde compound, a first solvent, the cyanoester and a first catalyst, and reacting to obtain the intermediate product; and S2, mixing the intermediate product with a second solvent, the double tin alkylation reagent DTBDT and a second catalyst, and reacting to obtain the double-capped micromolecule electron donor material.

9. The preparation method according to claim 8, wherein in the S1, a molar ratio of the dialdehyde compound to the cyanoester is 1:(5-6);

and, in the S1, a molar ratio of the dialdehyde compound to the first catalyst is 1:(0.1-0.2);

and, in the S1, the first solvent is selected from at least one of chloroform, dichloromethane, toluene, tetrahydrofuran or acetic acid;

and, in the S1, the first catalyst is selected from at least one of alumina, piperidine, ammonium acetate or triethylamine;

and, in the S1, a reaction temperature is 100-150° C., and a reaction duration is 4-10 h;

and, in the S1, after the reaction is finished, a reaction solution is decompressed and distilled out of the first solvent, and the intermediate product is obtained by silica gel column chromatography separation;

and, in the S2, a molar dosage ratio of the intermediate product to the double tin alkylation reagent DTBDT is (2.0-2.5):1;

and, in the S2, a molar dosage ratio of the intermediate product to the second catalyst is 1:(0.1-0.2);

and, in the S2, the second solvent is selected from at least one of dioxane, toluene, chlorobenzene or o-xylene;

and, in the S2, the second catalyst is selected from at least one of tetrapalladium (triphenylphosphine), tridibenzylideneacetone dipalladium or 1,1'-bis diphenyl phosphine ferrocene palladium dichloride;

and, in the S2, the reaction temperature is 100-200° C., and the reaction duration is 12-72 h;

and, in the S2, after the reaction is finished, the second solvent is distilled out of the reaction solution under reduced pressure, and the intermediate product is obtained by silica gel column chromatography separation.

10. A method of manufacturing the photovoltaic device of claim 6, comprising:

providing the double-capped micromolecule electron donor material; and forming an active layer that includes the double-capped micromolecule electron donor material and an electron acceptor, the active layer being disposed between two electrodes, thereby producing the photovoltaic device.

* * * * *